United States Patent
ReFaey et al.

(10) Patent No.: US 11,771,357 B2
(45) Date of Patent: Oct. 3, 2023

(54) RING-SHAPED CORTICAL ELECTRODE ASSEMBLY

(71) Applicant: Mayo Foundation for Medical Education and Research, Rochester, MN (US)

(72) Inventors: Karim ReFaey, Jacksonville, FL (US); William Tatum, Ponte Vedra Beach, FL (US); Alfredo Quinones-Hinojosa, Bel Air, MD (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 874 days.

(21) Appl. No.: 16/627,524

(22) PCT Filed: Jun. 28, 2018

(86) PCT No.: PCT/US2018/039956
§ 371 (c)(1),
(2) Date: Dec. 30, 2019

(87) PCT Pub. No.: WO2019/006094
PCT Pub. Date: Jan. 3, 2019

(65) Prior Publication Data
US 2020/0163567 A1    May 28, 2020

Related U.S. Application Data

(60) Provisional application No. 62/527,896, filed on Jun. 30, 2017.

(51) Int. Cl.
*A61B 5/24* (2021.01)
*A61B 5/00* (2006.01)
(Continued)

(52) U.S. Cl.
CPC ............ *A61B 5/24* (2021.01); *A61B 5/282* (2021.01); *A61B 5/291* (2021.01); *A61B 5/377* (2021.01);
(Continued)

(58) Field of Classification Search
CPC .......... A61B 5/24; A61B 5/282; A61B 5/291; A61B 5/377; A61B 5/4064; A61B 2562/04; A61N 1/0531; A61N 1/3605
See application file for complete search history.

(56) References Cited

U.S. PATENT DOCUMENTS

| | | |
|---|---|---|
| 4,903,702 A | 2/1990 | Putz |
| 8,644,903 B1 | 2/2014 | Osa et al. |

(Continued)

FOREIGN PATENT DOCUMENTS

| | | |
|---|---|---|
| WO | WO 2007/138598 | 12/2007 |
| WO | WO 2012/052986 | 4/2012 |
| WO | WO 2016/179094 | 11/2016 |

OTHER PUBLICATIONS

Berger and Ojemann, "intraoperative brain mapping techniques in neuro-oncology," Stereotact Funct Neurosurg, 58(1-4):153-61, 1992.
(Continued)

*Primary Examiner* — Christopher A Flory
(74) *Attorney, Agent, or Firm* — Fish & Richardson P.C.

(57) ABSTRACT

This document describes systems, methods, and devices for sensing electrical activity in a brain of a mammal Some aspects include a cortical electrode assembly configured, in use, to sense electrical activity at a surface of a brain, the assembly comprising: a ring-shaped substrate; and a plurality of electrical sensors affixed to the ring-shaped substrate, wherein the plurality of electrical sensors are spaced along (Continued)

the ring-shaped substrate so as to form a ring of electrical sensors that substantially encircle an aperture formed by the ring-shaped substrate.

16 Claims, 7 Drawing Sheets

(51) Int. Cl.
    *A61N 1/05*         (2006.01)
    *A61N 1/36*         (2006.01)
    *A61B 5/282*       (2021.01)
    *A61B 5/291*       (2021.01)
    *A61B 5/377*       (2021.01)

(52) U.S. Cl.
    CPC .......... *A61B 5/4064* (2013.01); *A61N 1/0531* (2013.01); *A61N 1/3605* (2013.01); *A61B 2562/04* (2013.01)

(56) References Cited

U.S. PATENT DOCUMENTS

| | | | |
|---|---|---|---|
| 2004/0176831 A1* | 9/2004 | Gliner | A61N 1/0531 607/142 |
| 2011/0029055 A1 | 2/2011 | Tidemand | |
| 2012/0277834 A1* | 11/2012 | Mercanzini | A61N 1/36125 607/116 |
| 2013/0090704 A1 | 4/2013 | Kolen et al. | |
| 2014/0277258 A1* | 9/2014 | Mercanzini | A61N 1/37211 607/45 |
| 2016/0074655 A1* | 3/2016 | Mercanzini | A61B 5/24 607/116 |
| 2016/0331968 A1 | 11/2016 | Greenberg et al. | |
| 2017/0347908 A1* | 12/2017 | Watanabe | A61B 5/25 |
| 2018/0043154 A1* | 2/2018 | Ejiri | A61N 1/0476 |

OTHER PUBLICATIONS

Berger et al., "Brain mapping techniques to maximize resection, safety, and seizure control in children with brain tumors," Neurosurgely, 25(5):786-92, 1989.

Eseonu et al., "Awake craniotomy vs craniotomy under general anesthesia for perirolandic gliomas: evaluating perioperative complications and extent of resection," Neurosurgery, 81(3):481-9, Sep. 2017.

Formaggio et al., "Frequency and time-frequency analysis of intraoperative ECoG during awake brain stimulation," Frontiers in neuroengineering, 6:1, Feb. 2013.

Hervey-Jumper et al., "Awake craniotomy to maximize glioma resection: methods and technical nuances over a 27-year period," J. Neurosurg., 123(2):325-39, 2015.

International Preliminary Report on Patentability in International Application No. PCT/US2018/039956 dated Dec. 31, 2019, 10 pages.

International Search Report & Written Opinion in International Application No. PCT/US2018/039956 dated Aug. 31, 2018, 27 pages.

Salam et al., "Subdural porous and notched mini-grid electrodes for wireless intracranial electroencephalographic recordings," Journal of multidisciplinary healthcare, 7:573, Dec. 2014.

Sanai and Berger, "Mapping the horizon: techniques to optimize tumor resection before and during surgery," Clin. Neurosurg, 55:14-9, 2008.

Sanai and Berger, "Operative techniques for gliomas and the value of extent of resection," Neurotherapeutics, 6(3):478-86, 2009.

Sanai et al., "Functional outcome after language mapping for glioma resection," N. Engl. J. Med., 358(1):18-27, 2008.

Voorhies and Cohen-Gadoi, "Techniques for placement of grid and strip electrodes for intracranial epilepsy surgery monitoring: Pearls and pitfalls," Surg. Neurol. Int., 4:98, Jun. 2013.

William J. Marks, Jr and Kenneth D. Laxer, Chapter 7—Invasive Clinical Neurophysiology in Epilepsy and Movement Disorders, In Aminoft's Electrodiagnosis in Clinical Neurology (Sixth Edition), edited by Michael J. Amino ff,, W.B. Saunders, London, 20 I 2, pp. 165-185, ISBN 9781455703081.

\* cited by examiner

RING-SHAPED CORTICAL ELECTRODE ASSEMBLY

CROSS-REFERENCE TO RELATED APPLICATIONS

This application is a National Stage application under 35 U.S.C. § of International Application No. PCT/US2018/039956, having an International Filing Date of Jun. 28, 2018, which claims priority to U.S. Application Ser. No. 62/527,896, filed on Jun. 30, 2017. The disclosures of the prior applications are considered part of the disclosure of this application, and are incorporated in their entirety into this application.

BACKGROUND

Electrocorticography (ECoG) is a neurophysiological technique that allow direct intraoperative electrical activity recording from the cerebral cortex. This technique was developed by Penfield and Jasper in the 1940s with the aim to help define the epileptogenic cortical region intraoperatively and to provide surgeons with a similar type of cerebral potential recording as the electroencephalogram (EEG), but with the elimination of interference from the scalp and skin.

SUMMARY

This document describes systems, methods, devices, and other techniques for intracranial monitoring of electrical activity of the brain using a ring-shaped cortical electrode assembly.

Some implementations of the subject matter disclosed herein include a cortical electrode assembly configured, in use, to sense electrical activity at a surface of the brain. The assembly can include a ring-shaped substrate and multiple electrical sensors affixed to the ring-shaped substrate. The electrical sensors can be spaced along the ring-shaped substrate so as to form a ring of electrical sensors that substantially encircle an aperture formed by the ring-shaped substrate.

Some implementations of the subject matter disclosed herein include an electrocortigraphy method that includes the steps of placing a cortical electrode assembly on a surface of a brain, applying an electrical stimulus to the surface of the brain, and measuring a response to the electrical stimulus based on signals generated by a plurality of electrical sensors of the cortical electrode assembly Various features and advantages of these techniques are described through the specification and will be apparent to one of ordinary skill in the field.

DESCRIPTION OF DRAWINGS

Like references and symbols among the drawings indicate like elements.

DETAILED DESCRIPTION

This document describes systems, methods, devices, and other techniques for intracranial monitoring of electrical activity of the brain. In some implementations, the monitoring is performed using a ring-shaped cortical electrode assembly having a set of sensors arranged in a ring-like formation. When the assembly is placed on the brain, the ring of sensors can encircle a target brain region, e.g., a region that has been identified as either probable epileptogenic region or tumorigenic area. A surgeon, physician, or other operator may use an external instrument to apply a localized electrical stimulus to the target brain region through the center opening of the electrode assembly. The stimulus may cause an electrical response (e.g., an immediate response and a subsequent after-discharge response of electrical activity) at or around the target brain region. Electrical activity of the response may propagate in one or more directions outward toward one or more of the sensors in the electrode assembly.

The ring-like configuration of sensors can facilitate detection and high-resolution localization of an electrical response to a stimulus. In contrast to some traditional cortical electrode assemblies that provide electrodes in an n×m grid or strip configuration, the ring-like configuration of the assemblies disclosed herein may permit detection of after-discharge electrical activity that propagates in any direction from the source location of the stimulus. In some implementations, the ring-like configuration may also provide improved intraoperative monitoring of brain electrical activity during certain procedures such as resection of a tumor or epileptogenic portion of the brain. For example, an operation may be performed through the aperture of the electrode assembly while the set of sensors surrounding the aperture continuously monitor electrical activity during the operation.

Figure 1:
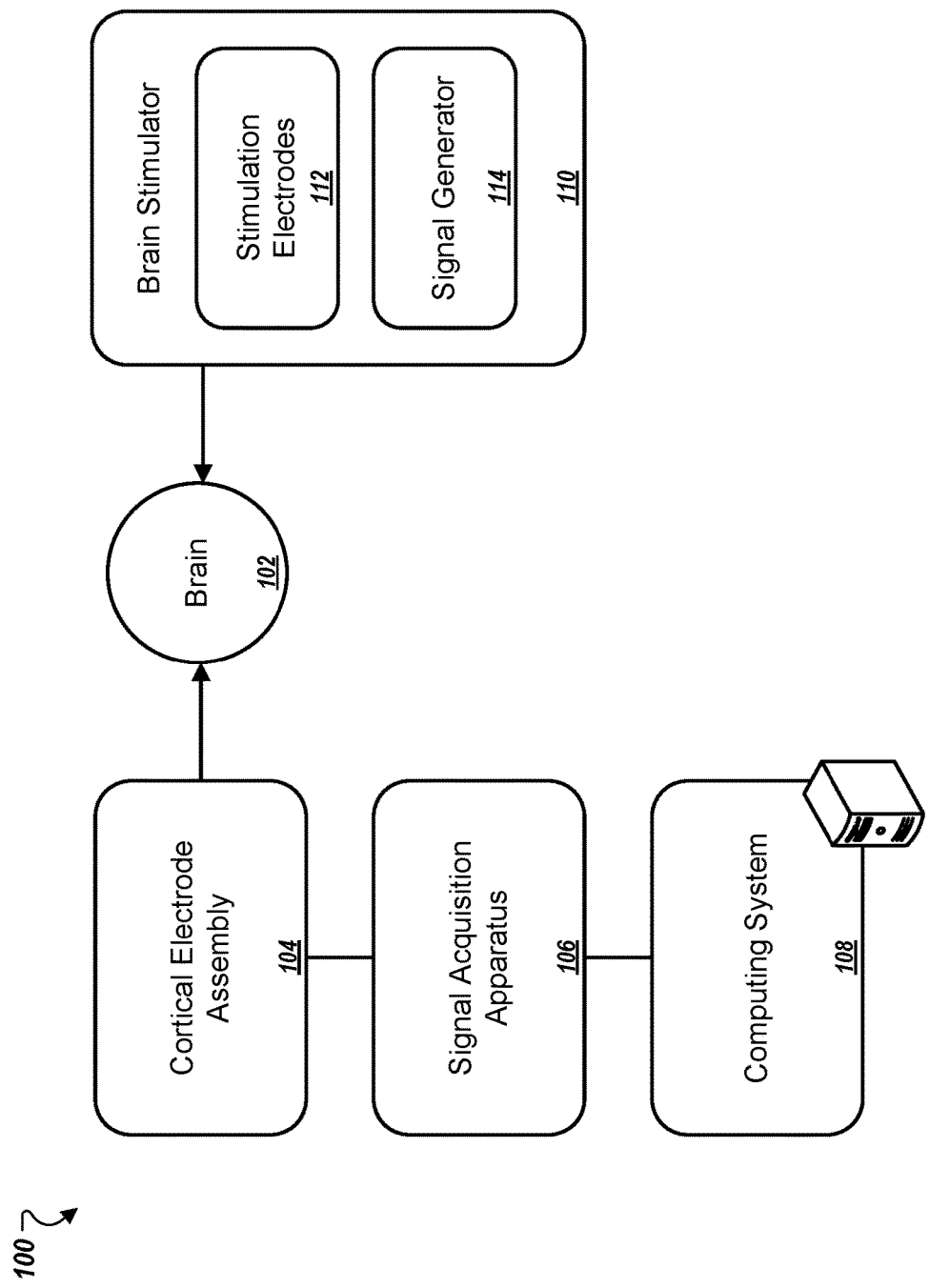
FIG. 1 is a conceptual diagram of an example environment for performing an electrocorticography procedure using a ring-shaped cortical electrode assembly.

Referring to FIG. 1, a conceptual diagram is depicted of an example environment 100 for performing an electrocorticography procedure. The environment 100 includes a ring-shaped cortical electrode assembly 104, a signal acquisition apparatus 106, a computing system 108, and a brain stimulator 110.

The electrode assembly 104 includes a collection of sensors that are configured in use to sense electrical activity of a brain 102 of a subject. In some implementations, the subject is a human such as an epilepsy patient undergoing an operation to obtain seizure control by resecting an area of the brain. In other implementations, the subject is another species of mammal or is non-mammalian. The electrode assembly 104 can generate electrical signals representative of electrical activity sensed at a surface of the brain (e.g., the cerebral cortex). Each sensor in the electrode assembly 104 may generate a respective signal to represent localized electrical activity for a focal region of the brain at or around the location of contact of the sensors on the surface of the brain. The respective signals for each sensor may be transmitted over corresponding sensor channels to the signal acquisition apparatus 106. Additional detail concerning the structure and features of a ring-shaped cortical electrode assembly is provided, for example, in FIG. 2A.

The signal acquisition apparatus 106 is configured to process and record electrical signals from the electrode assembly 104. In some implementations, leads from each sensor in the electrode assembly 104 are coupled to the signal acquisition apparatus 106. The signal acquisition apparatus 106 may amplify, filter, and/or de-noise the analog signals from each sensor. In some implementations, the signal acquisition apparatus 106 includes an analog-to-digital converted (ADC) to convert the pre-processed analog signals from the leads of the electrode assembly 104 to quantized digital data that can be processed by the computing system 108. In some implementations, the signal acquisition apparatus 106 can be embedded as a microcomputer or other miniaturized data processing apparatus that is embedded on the electrode assembly 104. The apparatus 106 may then communicate with computing system 108 via a physical link (e.g., wires or cables extending between 106 and 108) or via a wireless communication interface (e.g., BLUETOOTH or WI-FI). In other implementations, the signal acquisition apparatus 106 is distinct from the cortical electrode assembly 104 and is located a distance from the assembly 104. The leads from each of the sensors may extend to physically couple with the signal acquisition apparatus 106.

The acquired signals from the cortical electrode assembly 104, and pre-processed by the signal acquisition apparatus 106, may be further processed by a computing system 108. The computing system 108 can include one or more computers (e.g., data processing apparatus) in one or more locations. In some implementations, for example, the computing system 108 may include an electronic display (e.g., a computer monitor) that visualizes the electrical activity corresponding to each sensor of the cortical electrode assembly 104 by plotting the signals in real-time. The computing system 108 may provide alerts when abnormal activity is detected.

In some implementations, the environment 110 further includes a brain stimulator 110. The brain stimulator 110 includes a pair of stimulation electrodes 112 and a signal generator 114. The stimulation electrodes 112 can be disposed in a portion of the stimulator 110 that is configured to be held in a hand of a human operator and manipulated in free space. For example, the stimulation electrodes 112 may be provided in a surgeon-guided handheld bipolar stimulator with 2 ball-tip electrodes. In use, the surgeon can contact a surface of the subject's brain with the electrodes 112 and apply a localized electrical stimulus, e.g., in the target region of the brain encircled by the electrode ring of cortical electrode assembly 104. A signal generator 114 can drive the stimulation electrodes 112 with electrical pulses or a periodic waveform, for example, to apply a desired stimulus. In some implementations, the brain stimulator 110 is used to apply a superficial stimulus to a surface of the brain. In other implementations, the brain stimulator 110 is used to apply a deep stimulus to an interior portion of the brain. In some implementations, the brain stimulator 110 can be used for both superficial and deep stimulus.

Figure 2A:
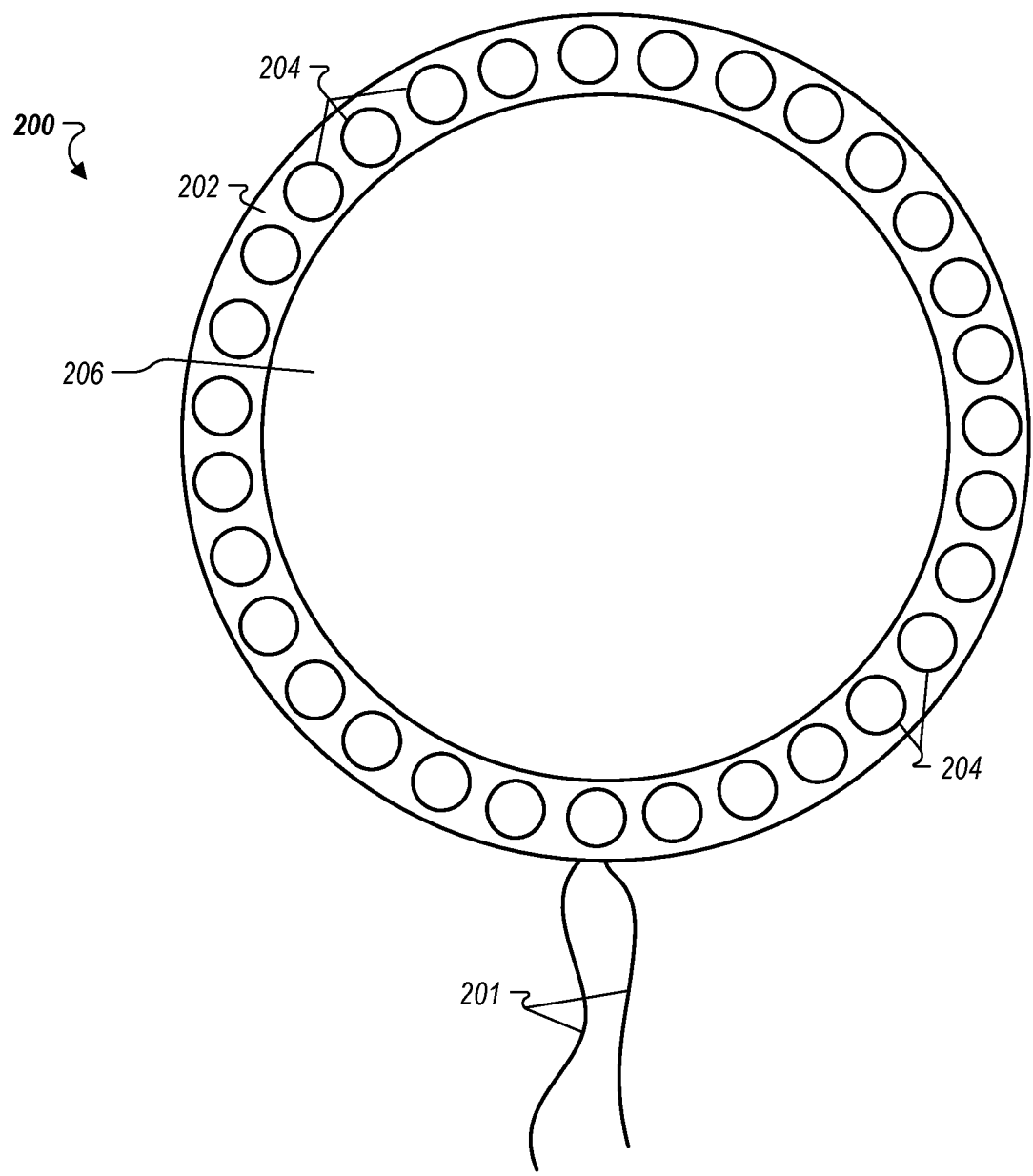
FIG. 2A is a diagram of an example ring-shaped cortical electrode assembly.

FIG. 2A is a diagram of an example ring-shaped cortical electrode assembly 200. The cortical electrode assembly 200 is configured to sense electrical activity at a surface of a brain in use, e.g., for intraoperative monitoring leading up to and during epilepsy surgery.

The assembly 200 includes a series of electrical sensors 204 arranged in the shape of a ring. The respective positions of the electrical sensors are fixed relative to each other in the assembly 200, thereby allowing a surgeon to lay the assembly and all of the electrical sensors at a desired location on the brain at once, rather than placing each sensor individually. In some implementations, the electrical sensors 204 are held in the ring shape by a substrate 202 to which each of the sensors 204 is affixed. In some implementations, the electrical sensors 204 may be held in the ring shape by a wire or other means that physically connects the sensors 204. The total number of electrical sensors 204 in the assembly 200 may vary depending on the size of the ring and the spacing between each sensor. However, it is typically desirable to minimize the size and spacing of each sensor 204, thereby minimizing inter-sensor gaps, maximizing the spatial resolution, and obtaining as close to 360 degree coverage as possible. For example, the number of sensors 204 in the assembly may be in the range 10 to 80 sensors, and preferably is in the range 20 to 50 sensors. The spacing between adjacent sensors may be in the range 2 millimeters (mm) through 8 mm.

Each of the electrical sensors 204 includes an electrical contact having an exposed surface arranged to contact a surface of the brain in use (e.g., the cerebral cortex). For example, the sensors 204 may be electrically conductive metallic contacts in the shape of a disc. The metallic contacts may be made of silver, platinum, stainless steel, or another conductive material that is safe for use on the brain. In some implementations, the metallic contacts have a diameter between 2 and 8 millimeters (mm), and preferably have a diameter between 3 and 5 mm.

The electrical sensors 204 are affixed to a substrate 202. The substrate 202 is in the shape of a ring and includes a band that forms a perimeter of the ring-shaped assembly 200 and an aperture 206 at the center of the band. The aperture 206 is open and generally free of interference from other structures of the assembly 200 that would hinder the ability of an operator to access a target brain region through the aperture 206, e.g., to apply a stimulation and/or to perform a surgery in the target brain region through the aperture 206. In some implementations, the outer diameter of the ring-shaped substrate 202 in the range 3 cm to 10 cm, and is preferably 4 or 5 cm. In some implementations, the inner diameter of the ring-shaped substrate 202 (i.e., the diameter of the aperture formed by the ring-shaped substrate) is in the range 2 cm to 9 cm, and is preferably 3 or 4 cm. The width of the substrate 202 may be slightly larger than the diameter of the electrical contacts for the sensors 204, e.g., from 0.4 to 1 cm, and preferably 0.5 cm. The substrate 202 may be relatively thin, e.g., between 0.3 and 0.8 mm.

The substrate 202 is generally constructed of an insulating material that can contact each of the electrical sensors 204 without shorting the sensors 204. Suitable substrate materials include silastic or silicone, for example. In general, the substrate 202 can be made of a flexible material so that it can conform to the contours of the brain in use. In some implementations, the electrical sensors 204 (e.g., the metallic contacts of the sensors 204) are glued or otherwise bonded to a surface of the substrate 202. In some implementations, the electrical sensors are embedded within the substrate 202 by a laminate construction that shields one side of each contact while exposing the opposite side of the contact so that it is accessible to contact the brain in use.

A lead 200 (e.g., a thin wire) can be attached to each electrical sensor 204 in the assembly 200 to carry electrical signals conducted by the sensors 204 to a signal acquisition apparatus. A separate sensor channel can be provided by each electrical sensor 204. The leads extending from each sensor 204 may be insulated and routed around the periphery of the assembly 200 (rather than through the aperture 206) to a focal point where the leads are bundled (201) and extend a distance to the signal acquisition apparatus.

In some implementations, the assembly 200 may include reference markings that allow surgeons or others to map individual sensors 204, or groups of sensors 204, to a location of the brain on which the assembly 200 has been placed. For example, a label may be printed or affixed on the substrate 202 adjacent to each one of the electrical sensors 204. The label may include a respective alphanumeric symbol, for instance, that uniquely identifies each sensor 204 or group of sensors 204. Thus, when the signal from each sensor is plotted for the user, the plot can be identified by the unique symbol for the sensor and a user can correlate the plot with a particular location of the brain where the sensor is placed.

Although in the example of FIG. 2A the assembly 200 is substantially circular, other shapes are also contemplated. For example, the ring may be elongated to form an oval, or an n-sided polygon (where n is at least 3) with a central opening (e.g., aperture 206) may also be suitable to capture electrical activity of the brain that emanates in any direction from a stimulation location near the center of the assembly 200. Additional non-linear configurations having a substantial central opening are also contemplated.

Figure 2B:
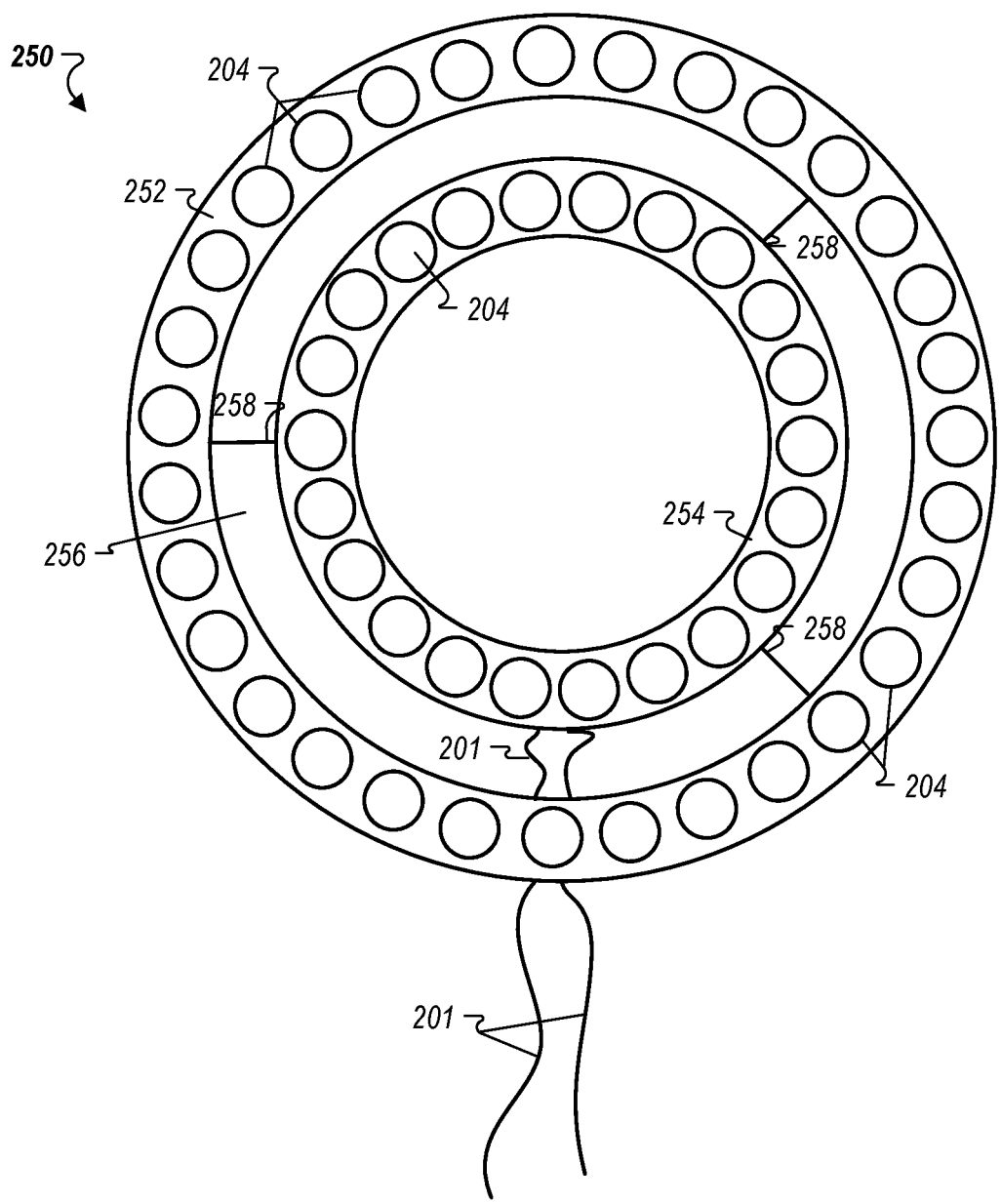
FIG. 2B is a diagram of an example ring-shaped cortical electrode assembly having multiple concentric rings.

In some implementations, the assembly 200 can include multiple concentric ring-shaped substrates that each have a respective set of sensors arranged in a ring around the respective substrate. A gap between each ring-shaped substrate may be sized to permit insertion of stimulation electrodes from a stimulator apparatus through the gap to facilitate cortical and/or subcortical brain mapping. For example, the assembly 200 may have three concentric ring-shaped substrates with inner diameters of 3, 6, and 9 centimeters, respectively. A 1 cm gap between each ring allows access to the target brain region for stimulation. In some implementations, the gap is in the range 0.5-2.5 cm, and is preferably 1 or 1.5 cm. The ring-shaped substrates may be fixedly or removably attached to each other by structures that link the respective rings to form a unitary assembly 200. In some implementations, the assembly 200 is modular. For example, different rings of different sizes may be snapped together or removed according to the needs of a surgeon. FIG. 2B depicts an example of a cortical electrode assembly 250 that includes two concentric rings 252 and 254 spaced from each other by gap 256. A bundle of leads 201 extends from the inner ring 254. In some implementations, one or more connecting structures 258 may span the gap 258 to secure the inner ring 254 relative to the outer ring 252. In some implementations, the cortical electrode assembly 250 depicted in FIG. 2B can be extended to include n concentric rings with a gap between each ring to permit placement of the tip of a stimulator apparatus in any of the gaps. The number of rings n can be 2, 3, 4, 5, or more, for example.

Figure 3:
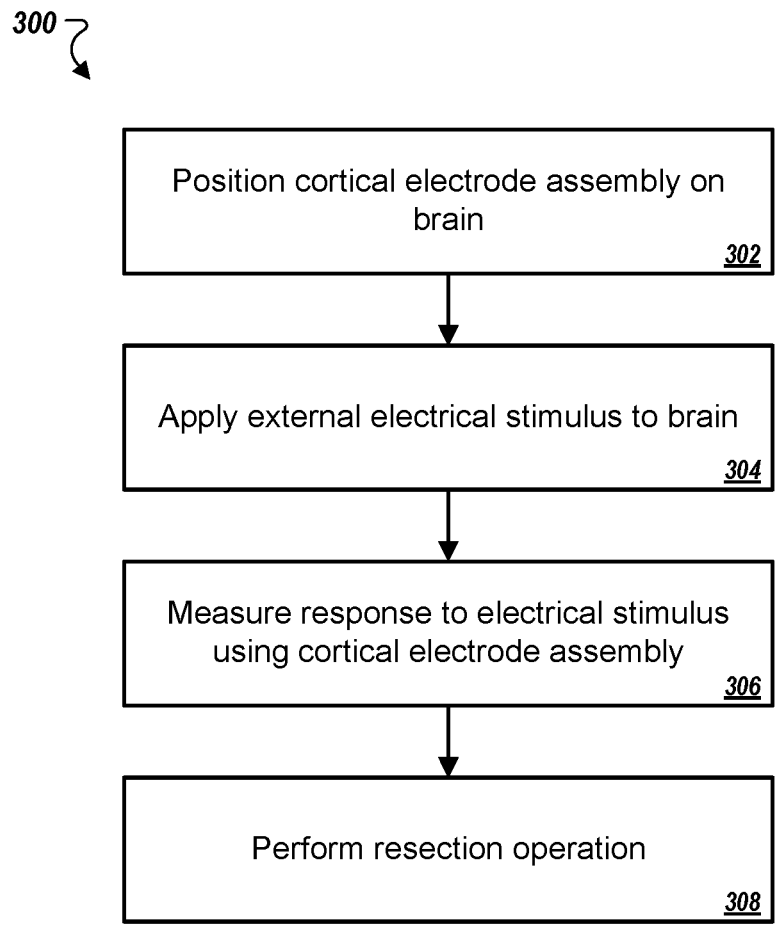
FIG. 3 is a flowchart of an example process for intraoperative monitoring of the electrical activity at the surface of a brain using a ring-shaped cortical electrode assembly.
Figure 4:
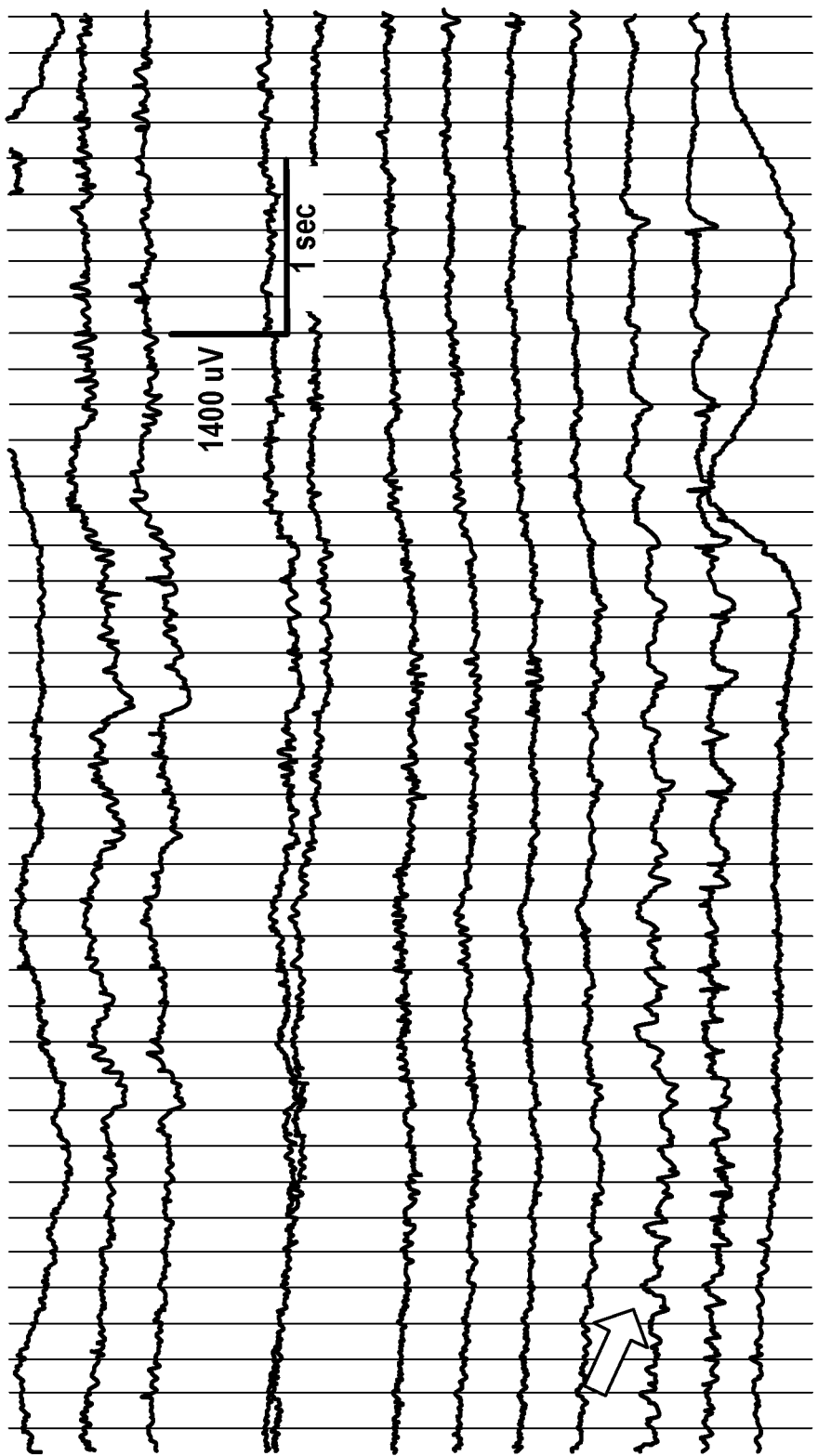
FIG. 4 is a plot of multiple channels of sensor data showing the after-discharge signals recorded by a prototype ring-shaped cortical electrode assembly.

FIG. 3 is a flowchart of an example process 300 for intraoperative monitoring of the electrical activity at the surface of a brain using a ring-shape cortical electrode assembly 200. At stage 302, an operator (e.g., a surgeon) positions the electrode assembly over a brain region of interest, e.g., following a craniotomy that removes a section of skull to provide direct access to the brain. The region of interest may be estimated as a likely epileptogenic region or the site of a tumor, for example. At stage 304, the operator applies an external electrical stimulus to the brain, e.g., using a stimulator with 2 ball-tip electrodes. The stimulus may be applied near the electrode assembly and preferably within the central opening (aperture) of the assembly. At stage 306, a response to stimulus is measured using signals sensed by electrodes in the ring-shaped electrode assembly. The results of the response can be used to guide a surgeon's actions during an operation at stage 308, such as to remove (resect) a tumor or epileptogenic region of the brain. In some implementations, continuous monitoring may occur during the operation in order to identify markers of an impending intraoperative seizure.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

Example 1

Figure 5A:
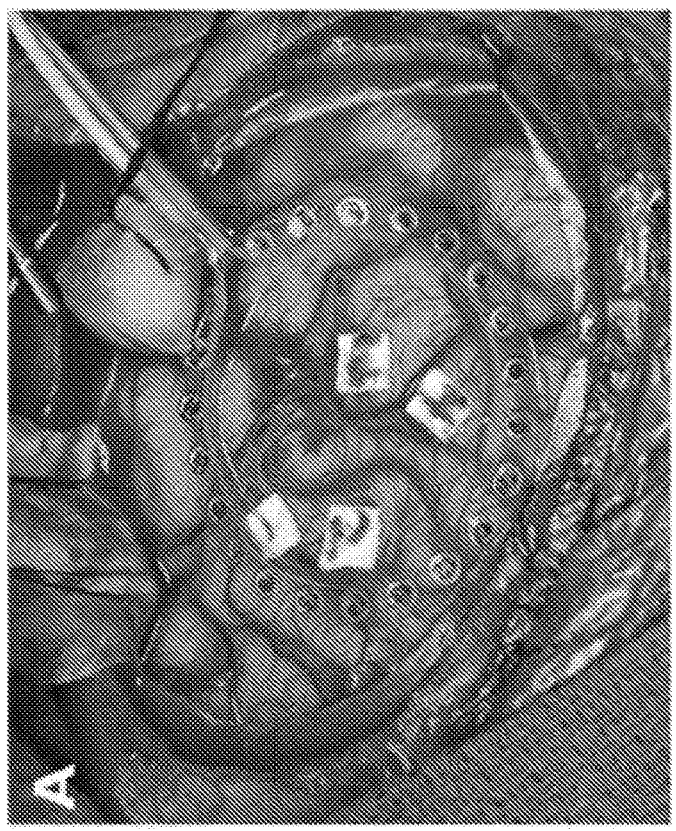
FIGS. 5A and 5B are photographs of the prototype ring-shaped cortical electrode assembly in use.
Figure 5B:
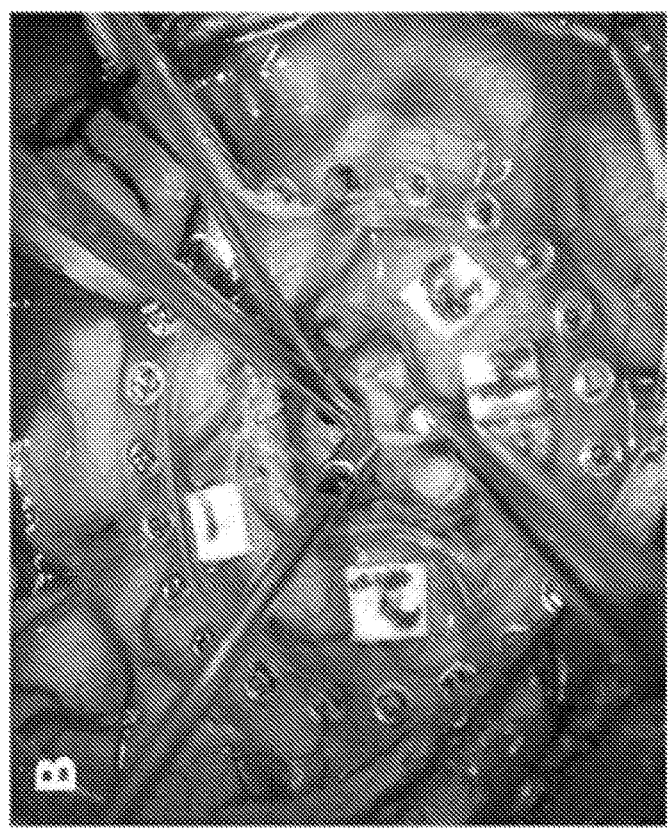
Figure 6B:
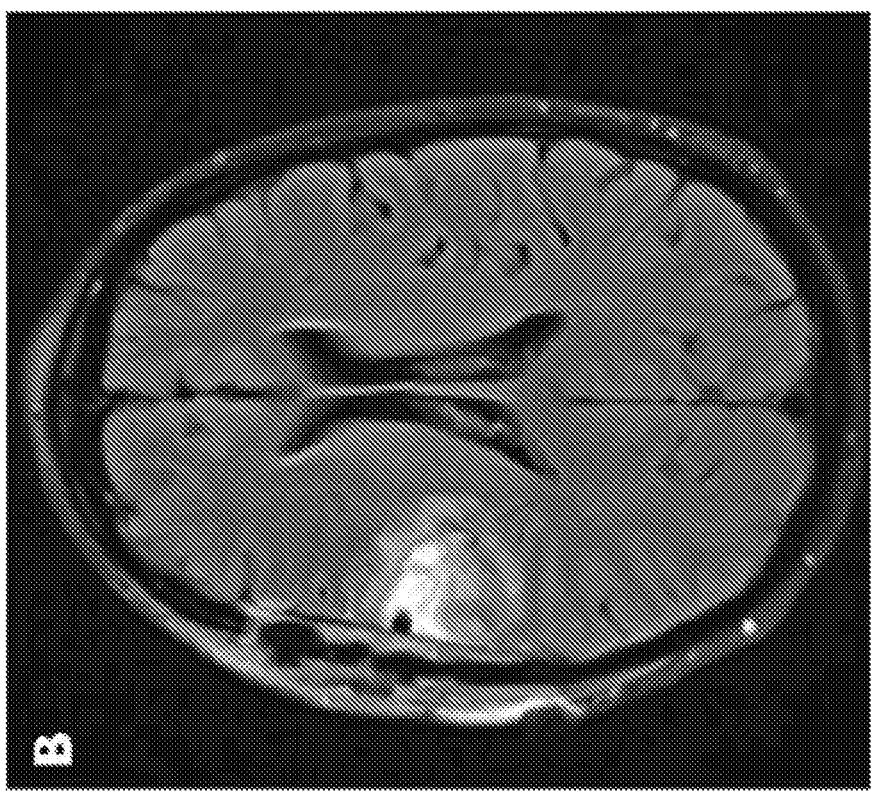
FIG. 6B is a non-contrast enhancing FLAIR sequence imaging showing postoperative fluid in the resection cavity.
Figure 6A:
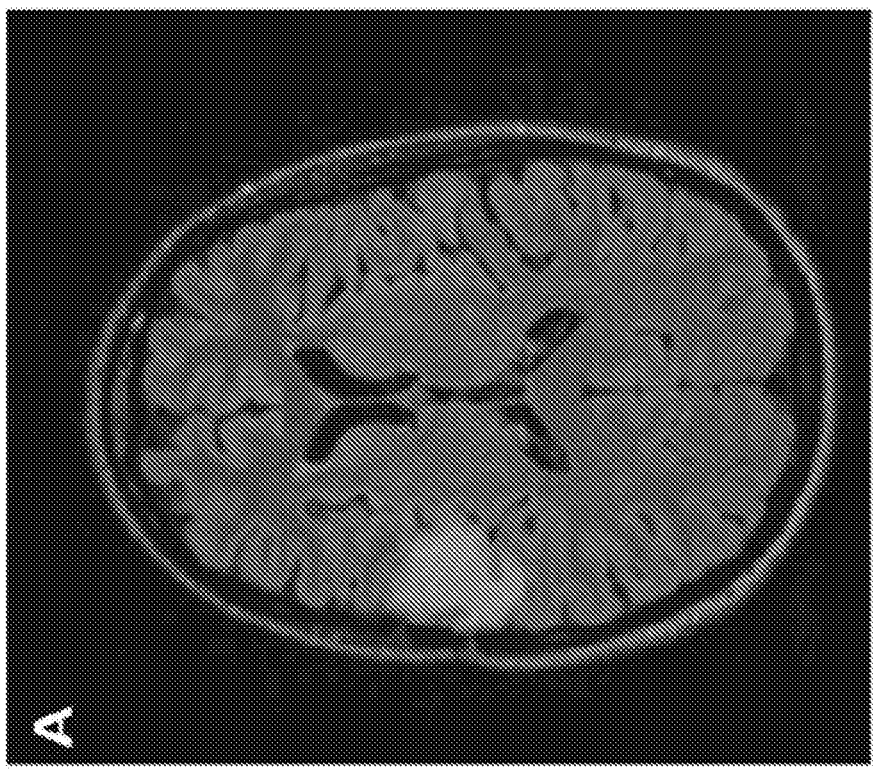
FIG. 6A is a non-contrast enhancing FLAIR lesion involving the right inferior Frontal gyrus adjacent to the Sylvian fissure with focal mass effect on the sulci and involvement of both the gray and white matter in this region.

A prototype ring-shaped cortical electrode assembly was tested in the operating room on a series of five patients that were diagnosed with brain tumors and/or epileptogenic symptoms. In one case, a 53-year old patient with known history of oligodendroglioma grade II that was diagnosed in 2009 after a biopsy. The patient has followed up with a series of MRIs since the diagnosis. The MRI showed a progressive non-contrast enhancing FLAIR lesion involving the right inferior frontal gyrus adjacent to the sylvian fissure with focal mass effect on the sulci and involvement of both the gray and white matter in this region (FIG. 6A). The patient was taken to the operating room for an awake craniotomy. After opening of the dura, surgeons placed the ring-shaped cortical electrode assembly for recording the afterdischarge responses (FIG. 5A) while the brain mapping using an Ojemann cortical stimulator (from Integra Lifesciences). The sensory function for the mouth and the back of the tongue were identified at 3 mA stimulation and were confirmed by repeated trials of stimulation. A 3 mm corridor was identified as a safe entry zone, which corticectomy was performed (FIG. 5B). The tumor was removed in a piece meal fashion while the patient was awake and counting from zero to one hundred. The patient tolerated the surgery well with no complications. The post operative MRI showed near gross total resection (FIG. 6B) and the patient was discharged home on postoperative day two without a neurological deficit.

What is claimed is:

1. A cortical electrode assembly configured, in use, to sense electrical activity at a surface of a brain, the assembly comprising:
    a plurality of ring-shaped substrates in a concentric arrangement; and
    for each ring-shaped substrate of the plurality of ring-shaped substrates, a respective plurality of electrical sensors affixed to the ring-shaped substrate, the respective plurality of electrical sensors spaced along the ring-shaped substrate so as to form a respective ring of electrical sensors on the ring-shaped substrate,
    wherein the respective plurality of electrical sensors affixed to a first ring-shaped substrate of the plurality of ring-shaped substrates encircle an aperture formed by the first ring-shaped substrate,
    wherein the plurality of ring-shaped substrates are spaced apart from each other so as to form respective gaps between each successive pair of ring-shaped substrates in the concentric arrangement through which stimulation electrodes can be inserted to facilitate cortical or subcortical brain mapping.

2. The cortical electrode assembly of claim 1, wherein each of the respective plurality of electrical sensors affixed to the first ring-shaped substrate comprises an electrically conductive contact configured to contact the surface of the brain in use.

3. The cortical electrode assembly of claim 2, wherein the electrically conductive contacts are metallic contacts.

4. The cortical electrode assembly of claim 2, wherein:
    the electrically conductive contacts of the respective plurality of electrical sensors affixed to the first ring-shaped substrate are each disc-shaped; and
    a diameter of each of the electrically conductive contacts is in the range 2 millimeters (mm) through 8 mm.

5. The cortical electrode assembly of 2, wherein adjacent electrically conductive contacts for at least a subset of the respective plurality of electrical sensors affixed to the first ring-shaped substrate are spaced apart on the first ring-shaped substrate from their centers by a distance in the range 2 millimeters (mm) through 8 mm.

6. The cortical electrode assembly of claim 5, wherein the subset of the respective plurality of electrical sensors includes at least a majority of the respective plurality of electrical sensors.

7. The cortical electrode assembly of claim 5, wherein the subset of the respective plurality of electrical sensors includes all of the respective plurality of electrical sensors.

8. The cortical electrode assembly of claim 2, wherein a total number of electrical sensors in the respective plurality of electrical sensors affixed to the first ring-shaped substrate is in the range of 10 electrical sensors through 80 electrical sensors.

9. The cortical electrode assembly of claim 1, wherein the first ring-shaped substrate comprises an insulating material that is configured to prevent electrical sensors affixed to the first ring-shaped substrate from electrically shorting in use.

10. The cortical electrode assembly of claim 1, wherein the first ring-shaped substrate is substantially circular.

11. The cortical electrode assembly of claim 1, wherein an outer diameter of the first ring-shaped substrate is in the range 3 centimeters (cm) to 10 cm.

12. The cortical electrode assembly of claim 11, wherein an inner diameter of the first ring-shaped substrate is in the range 2 cm to 9 cm.

13. The cortical electrode assembly of claim 1, further comprising a plurality of leads extending from the respective plurality of electrical sensors on each of the plurality of ring-shaped substrates, the plurality of leads configured to transmit electrical signals representative of electrical activity sensed at the surface of the brain to a signal acquisition apparatus.

14. The cortical electrode assembly of claim 13, wherein the plurality of leads are routed around the aperture formed by the first ring-shaped substrate so that the aperture is clear of interference that would prevent an operator to access a surface of the brain via the aperture in use.

15. The cortical electrode assembly of claim 1, wherein each of the plurality of ring-shaped substrates is shaped substantially as an oval or an n-sided polygonal ring, wherein n is at least 3.

16. An electrocorticography method, comprising:
    placing a cortical electrode assembly on a surface of a brain;
    applying an electrical stimulus to the surface of the brain; and
    measuring a response to the electrical stimulus based on signals generated by electrical sensors of the cortical electrode assembly,
    wherein the cortical electrode assembly includes:
        a plurality of ring-shaped substrates in a concentric arrangement; and
        for each ring-shaped substrate of the plurality of ring-shaped substrates, a respective plurality of electrical sensors affixed to the ring-shaped substrate, the respective plurality of electrical sensors spaced along the ring-shaped substrate so as to form a respective ring of electrical sensors on the ring-shaped substrate,
        wherein the respective plurality of electrical sensors affixed to a first ring-shaped substrate of the plurality of ring-shaped substrates encircle an aperture formed by the first ring-shaped substrate,
        wherein the plurality of ring-shaped substrates are spaced apart from each other so as to provide respective gaps between each successive pair of ring-shaped substrates in the concentric arrangement through which stimulation electrodes can be inserted to facilitate cortical or subcortical brain mapping.

* * * * *